US009222870B2

(12) United States Patent
Di Carlo et al.

(10) Patent No.: US 9,222,870 B2
(45) Date of Patent: Dec. 29, 2015

(54) METHOD AND DEVICE FOR MULTI-PARAMETER IMAGING WITHIN A SINGLE FLUORESCENT CHANNEL

(75) Inventors: Dino Di Carlo, Los Angeles, CA (US); Daniel R. Gossett, Los Angeles, CA (US); Westbrook M. Weaver, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 686 days.

(21) Appl. No.: 13/316,294

(22) Filed: Dec. 9, 2011

(65) Prior Publication Data
US 2012/0148140 A1 Jun. 14, 2012

Related U.S. Application Data

(60) Provisional application No. 61/422,073, filed on Dec. 10, 2010.

(51) Int. Cl.
*C12N 5/00* (2006.01)
*G01N 15/14* (2006.01)
*G01N 1/31* (2006.01)
*G01N 15/10* (2006.01)

(52) U.S. Cl.
CPC .............. *G01N 15/1468* (2013.01); *G01N 1/31* (2013.01); *G01N 2015/1006* (2013.01)

(58) Field of Classification Search
None
See application file for complete search history.

(56) References Cited

U.S. PATENT DOCUMENTS

| | | | | |
|---|---|---|---|---|
| 4,745,285 A * | 5/1988 | Recktenwald et al. | .... | 250/458.1 |
| 5,294,749 A * | 3/1994 | Lauder et al. | .................. | 174/535 |
| 6,049,380 A * | 4/2000 | Goodwin et al. | ............. | 356/317 |
| 2002/0081014 A1* | 6/2002 | Ravkin | ........................... | 382/134 |
| 2004/0246478 A1* | 12/2004 | Zimmermann et al. | ....... | 356/318 |
| 2008/0213915 A1* | 9/2008 | Durack et al. | .................. | 436/172 |
| 2010/0003666 A1 | 1/2010 | Lee et al. | | |
| 2010/0150423 A1* | 6/2010 | Hong et al. | .................... | 382/133 |
| 2010/0285487 A1* | 11/2010 | Rothbauer et al. | ................. | 435/6 |

FOREIGN PATENT DOCUMENTS

WO WO2011049965 A1 4/2011

OTHER PUBLICATIONS

Levenson et al., ILAR J., 49(1):78-88 (2008).*

(Continued)

*Primary Examiner* — Renee Claytor
*Assistant Examiner* — Thomas J Visone
(74) *Attorney, Agent, or Firm* — Vista IP Law Group LLP

(57) ABSTRACT

A method of monitoring temporal and spatial information of cells includes trapping a plurality of cells within single cell traps contained in a microfluidic device having an inlet, and an outlet. A first fluorescent stain specific to a first target is flowed into the inlet of the device and exposed to the trapped cells. The trapped cells are then imaged as a function of time. A fluorescent stain specific to a different target is flowed into the inlet of the device, the subsequent fluorescent stain having an emission spectrum that substantially overlaps with the emission spectrum of the prior fluorescent stain. The plurality of trapped cells are then imaged again as a function of time. The process can be repeated with additional fluorescent stains having substantially overlapping emission spectra. Images may be subtracted to reveal the contribution of a single fluorescent stain.

17 Claims, 9 Drawing Sheets

(56) References Cited

OTHER PUBLICATIONS

Su et al., Biotech. Bioeng., 102(3):856-868 (2009).*
Aramas et al., Anal. Chim. Acta, 471:176-186 (2002).*
Di Carlo et al., Anal. Chem, 7920-7926 (2006).*
Dickenson et al., Biotech., 31(6):1272-1278 (2001).*
Gould et al., Nature Prot., 4(3):291-308 (2009).*
Nilsson et al., Anal. Chim. Acta, 649:141-157 (2009).*
Ozcan et al., Lab Chip, 8:98-106 (2008).*
Rettig et al., Anal. Chem., 77:5628-5634 (2005).*
Schlachter et al., Opt. Exp., 17(25):22747-22760 (2009).*
Subach et al., Nature Meth., 6(2):153-159 (2009).*
Zhang et al., Anal. Chim. Acta. 556:171-177 (2006).*
Zimmermann et al., FEBS Let., 546:87-92 (2003).*
Pamp et al (Cytometry Part A, 75A: 90-103 (2009).*
Wahlby et al (Cytometry, 47:32-41 (2002).*
Vickerman et al., Lab Chip, 8:1468-1477 (2008).*
Coskun et al., Wide field-of-view lens-free fluorescent imaging on a chip, Lab Chip, 10, 824-827 (2010).
Hsieh et al., High speed detection of circulating tumor cells, Biosensors and Bioelectronics, 21 1893-99 (2006).
Schonbrun et al., High-throughput fluorescence detection using an integrated zone-plate array, Lab Chip, 10, 852-856 (2010).
Wang et al., Trapping cells on a stretchable microwell array for single-cell analysis, Anal. Bioamal Chem, DOI 10:1007/s00216-011-5535-9 (8 pages).
Di Carlo et al., Single-Cell Enzyme Concentrations, Kinetics, and Inhibition Analysis Using High-Density Hydrodynamic Cell Isolation Arrays, Anal. Chem 78, 4925-4930 (2006).

* cited by examiner

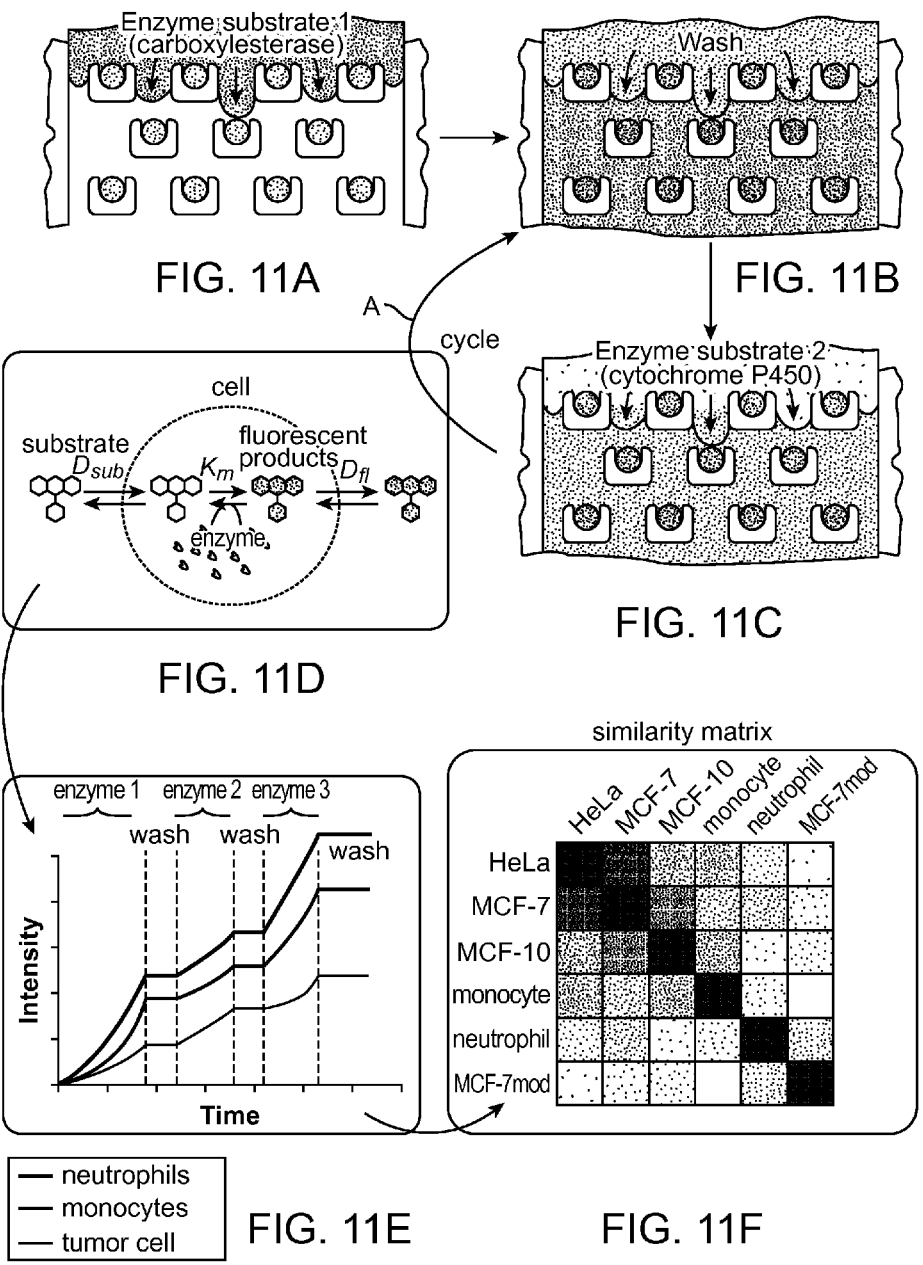

METHOD AND DEVICE FOR MULTI-PARAMETER IMAGING WITHIN A SINGLE FLUORESCENT CHANNEL

RELATED APPLICATION

This Application claims priority to U.S. Provisional Patent Application No. 61/422,073 filed on Dec. 10, 2010. Priority is claimed pursuant to 35 U.S.C. §119. The above-noted Patent Application is incorporated by reference as if set forth fully herein.

FIELD OF THE INVENTION

The field of the invention generally relates to methods and devices for imaging of cells. More particularly, the field of the invention pertains to high content imaging for the quantification of temporal and spatial information about cellular processes.

BACKGROUND

High content screening (i.e., automated microscopy and image analysis) is a powerful tool for drug discovery, diagnostics, and biomedical research. Automated measurement of temporal and spatial information about targeted cellular processes can help elucidate important cellular information. For instance, such information can provide important data regarding drug-target interactions in vitro. Another example is the identification of the presence of rare abnormal cells (e.g., metastatic cancer cells) in a tissue or blood. High content screening also offers the potential to enable high-throughput experimentation.

Bulk measurement tools such as plate readers or Western blots have been used in obtaining cellular information but these tools often provide misleading averages of populations and mask behaviors of rare abnormal cells or subpopulations. Microscopy techniques, in contrast, are compatible with living cells, and working with biomolecules in their cellular microenvironment provides more accurate information about individual cell function and molecular mechanisms. Unfortunately, the throughput of manual single-cell microscopy measurements is low. Automation can increase the quantity of measurements and enhance reproducibility by limiting user bias. Current approaches to automation through robotics (used for high content screening) have, however, been cost prohibitive and remain out of reach for point-of-care diagnostics, personalized medicine, and academic use. Further, the number of independent parameters that can be measured with these tools can be limited by overlap of fluorescence spectra.

Immunophenotyping, for example identifying T-cell subpopulations, stemness, or circulating cancer cells, often requires the identification of multiple biochemical parameters. Moreover, dynamic processes such as drug permeability through a cell monolayer may be best characterized by a temporal parameter.

While there is much effort toward expanding the capabilities of the scanning optical microscopes and other currently used cytometric methods, such as flow cytometry, several other tools and techniques are being developed which aim to bring down cost and expand access through miniaturization and simplification. For instance, high-throughput, parallel fluorescence detection has been achieved by an integrated zone-plate array. See Schonbrun et al., High-throughput fluorescence detection using an integrated zone-plate array, Lab Chip, 10, 852-856 (2010). As another example, fiber-optic array scanning technology has been developed that can scan substrates 500 times faster than conventional scanning microscopy. See Hsieh et al., High speed detection of circulating tumor cells, Biosensors and Bioelectronics, 21 1893-99 (2006). Yet another alternative to mechanical scanning lens-based systems that has been developed is the wide field-of-view lens-free fluorescent imaging of micro-objects or labeled cells. See Coskun et al., Wide field-of-view lens-free fluorescent imaging on a chip, Lab Chip, 10, 824-827 (2010). This compact technology has achieved ~10 µm spatial resolution over an 8-cm$^2$ field-of-view with a single image. While some of these techniques are well equipped to identify rare, single-cell events, however, positive and negative identifications may require a composite overlay of several signals demonstrating co-localization and some of these techniques are currently limited to a single wavelength.

Thus, while powerful imaging instruments have been developed, these have been limited by the overlap of fluorescent emission spectra or the devices are limited to a single wavelength. There remains a need for a method and system that is able to identify co-localized parameters in a manner that is not limited by spectral overlap.

SUMMARY

In one embodiment, a system is provided that is able to extract spatial and temporal information about several intracellular components using a single fluorescent channel, thereby eliminating the problem of overlapping fluorescence emission spectra. The system involves a microfluidic device that is configured to trap individual cells. The cells may be stained a plurality of times with different fluorescent labels all sharing the same fluorescence excitation and emission spectrum. The cells are imaged in real-time to enable measurements of temporal localization of cellular components and intracellular reaction kinetics. Examples include using markers to analyze the quantity of nucleic acid (e.g., DNA), comparison of nucleus-to-cytoplasm ratio, as well as glycosylation of surface proteins. Imaging techniques that may be used in conjunction with the system including imaging technologies such as wide field-of-view lens-free fluorescent imaging, fiber-optic array scanning technology, and microlens arrays.

In another embodiment, a method of monitoring temporal and spatial information of cells includes (a) trapping a plurality of cells within single cell traps contained in a microfluidic device having an inlet, and an outlet; (b) flowing a fluorescent stain specific to a first target into the inlet of the device; (c) imaging the plurality of trapped cells a plurality of times; (d) flowing a fluorescent stain specific to a different target into the inlet of the device, the fluorescent stain specific to a different target having an emission spectrum that substantially overlaps with the emission spectrum of the fluorescent stain of (b); and (e) imaging the plurality of trapped cells a plurality of times.

In still another embodiment, a system for monitoring temporal and spatial information of cells includes a microfluidic device having an inlet, an outlet, and a plurality single cell traps contained therein. A pump is operatively coupled to one of the inlet and the outlet. The system includes a plurality of fluorescent stains specific to different targets each having an emission spectrum that substantially overlaps with each other and a fluorescent excitation source. The system includes an imager device configured to image the plurality of trapped cells a plurality of times over a period of time.

BRIEF DESCRIPTION OF THE DRAWINGS

FIG. 1B illustrates a holographic imager platform for wide field-of-view simultaneous imaging of individual cells within the array.

FIGS. 11A-11C illustrate one method of performing single cell enzyme profiling.

FIG. 11D schematically illustrates an enzyme substrate reacting with an intracellular enzyme to form a fluorescent product.

FIG. 11E illustrates fluorescent intensity graphs as a function of time for three different cell types being sequentially exposed to three different enzyme substrates.

FIG. 11F illustrates a similarity matrix of various cell types.

DETAILED DESCRIPTION OF THE ILLUSTRATED EMBODIMENTS

Figure 1A:
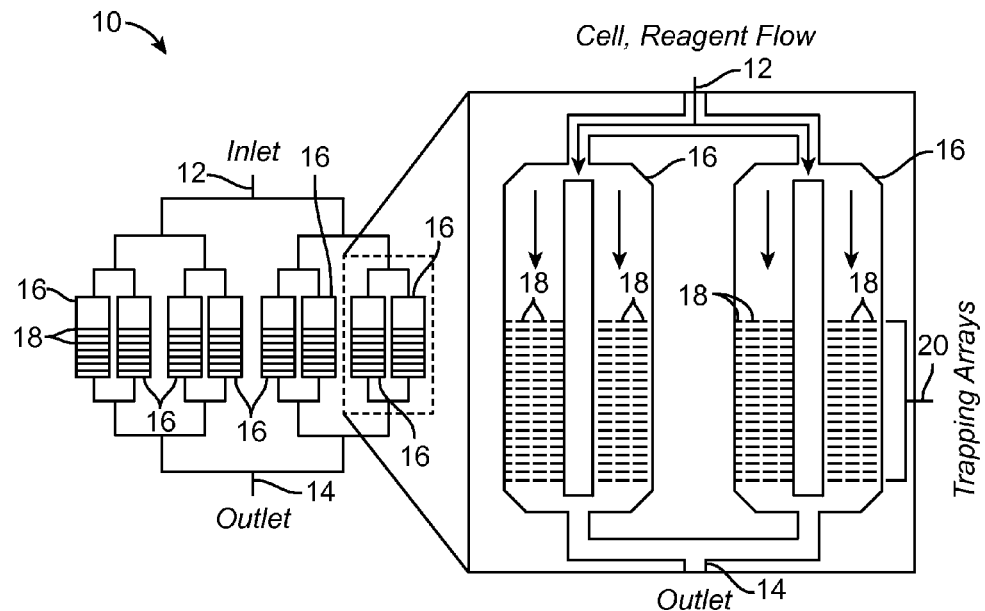
FIG. 1A illustrates a microfluidic device that includes a plurality of traps for capturing single cells therein. The microfluidic device includes a plurality of chambers each having an array of traps therein.

FIG. 1A illustrates a microfluidic device 10 according to one embodiment of the invention. The microfluidic device 10 includes at least one inlet 12, at least one outlet 14, and at least one flow chamber 16 containing therein a plurality of single cell traps 18 (or single particle traps in the event particles are trapped). The single cell traps 18 illustrated in FIG. 1A may be, in one embodiment, hydrodynamic traps that are weir-traps in which individual cells or other particles of interest are individually trapped therein. These "hydrodynamic" single cell traps 18 are illustrated in FIGS. 3, 4A, 4B, 5, 11A, 11B, and 11C. Thus, reference is made herein to hydrodynamic traps which are one type of single cell trap 18. However, it should be understood that other types of single cell traps 18 could be employed in conjunction with the inventive concepts described herein. For example, sticky or adhesive surfaces capable of trapping single cells or particles could be used. As yet another alternative, flexible, polydimethylsiloxane (PDMS)-based elastically stretchable traps may be used. The later type of single cell trap 18 is disclosed in Wang et al., Trapping cells on a stretchable microwell array for single-cell analysis, Anal Bioanal Chem, November, 2011, which is incorporated by reference as if set forth fully herein.

Figure 3:
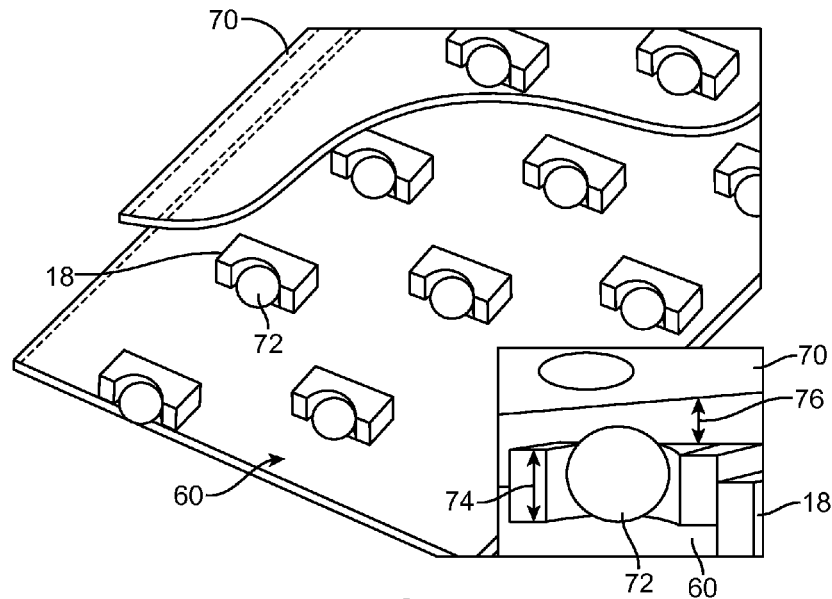
FIG. 3 illustrates a perspective view of a chamber containing an array of traps therein.

In FIG. 1A, eight (8) separate flow chambers 16 are illustrated but more or less may be used. Increasing the number of flow chambers 16 enables use of large numbers of single cell traps 18 in a massively parallel format. The microfluidic device 10 may be made using any number of structures commonly used in microfluidic devices. For example, the microfluidic device 10 may be formed as a two-part bonding structure with hydrodynamic traps 18 formed in a polydimethylsiloxane (PDMS) layer that is then bonded to a substrate such as glass, silicon or the like. This construction is seen in FIG. 3.

The single cell traps 18 may form an array 20 or multiple arrays 20 that include a plurality of individual single cell traps 18. In one embodiment, the single cell traps 18 are hydrodynamic weir-traps that are designed to be a sufficient size to capture or trap cells or analytes within a fluid flowing through the flow chambers 16. Additional details regarding exemplary hydrodynamic weir-traps that may be used as single cell traps 18 can be found in U.S. Patent Application Publication No. 2010-0003666 which is incorporated by references as if set forth fully herein.

Figure 1B:
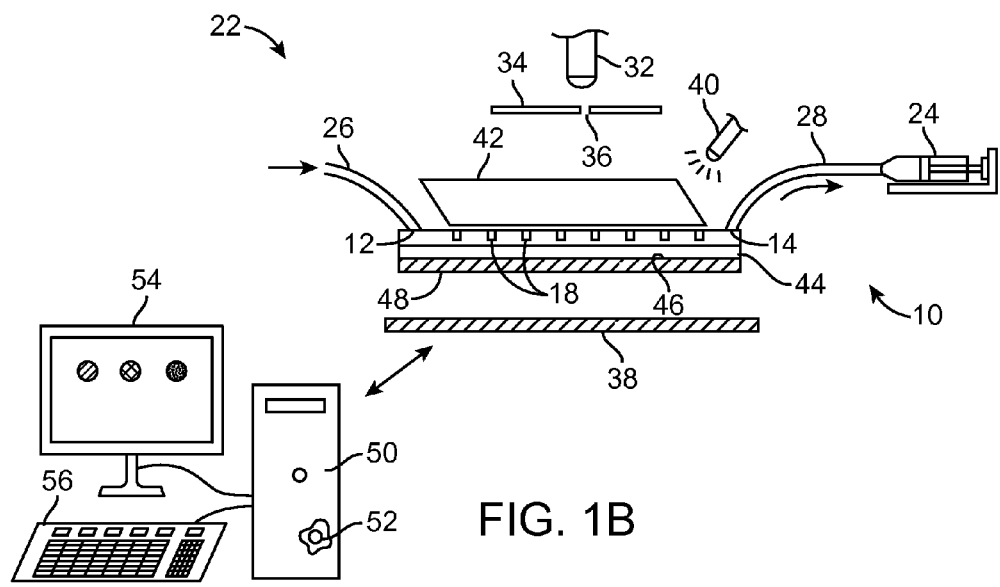
FIG. 1B illustrates a microfluidic device integrated with an imager device.

FIG. 1B illustrates a system 22 that includes the microfluidic device 10 of claim 1. The microfluidic device 10 includes a pump 24 such as a syringe pump that can be used to initiate flow through the microfluidic device 10. The pump 24 may be placed at the outlet 14 of the microfluidic device 10 or, alternatively, the pump 24 may be placed at the inlet 12 of the microfluidic device 10. Flow driven by capillarity may also be used as the pumping mechanism. The pump 24 is used to establish a flow of solution containing cells or particles for trapping within the single cell traps 18. The pump 24 is also used to flow various other solutions through the microfluidic device 10. These include wash solutions such as PBS as well as fluorescent stains as described below. In one aspect, a conduit 26 that is coupled to the inlet 12 may be selectively switched between different fluid solutions (e.g., fluid containing cells, wash, fluorescent stain solution). This may be accomplished using valves or the like commonly used in microfluidic devices. Alternatively, the conduit 26 may be omitted and a droplet (or multiple) droplets may be placed directly over the inlet 12 which is then drawn into the microfluidic device 10 via the pump 24 operatively coupled to the outlet via conduit 28.

The embodiment of FIG. 1B includes an imager 30. The imager 30 may include any number of imaging modalities. For example, a conventional optical microscope may be used although conventional optical microscopes are limited by the relatively small field-of-view. Given that the microfluidic device 10 will likely have a large number of flow chambers 16 and arrays 20 of single cell traps 18 contained therein, an imager 30 having a wide field-view is preferred. FIG. 1B illustrates an imager 30 that is a fluorescent imager that provides a very wide field-of-view without the use of any lenses. This imager 30 includes an illumination source 32 which is an incoherent light source or partially incoherent light source. The illumination source 32 is used as for the holographic imaging of the trapped particles or cells. For example, this illumination source 32 may be used to obtain bright field images of the cells. Light emitting diodes (LEDs) are one example of an illumination source 32 that can be used. LEDs are relative inexpensive, durable, and have generally low power requirements. Still referring to FIG. 1B, a spatial filter 34 is interposed between the illumination source 32 and the microfluidic device 10. The spatial filter 34 has an aperture 36 that permits the passage of light. The diameter is typically in the range of 50 μm to about 100 μm.

An image sensor 38 is disposed on an opposing side of the microfluidic device 10. The image sensor 38 is used to obtain the shadow or holographic images of the cells or particles trapped within the traps 18. The image sensor 38 may comprise, for example, a charged coupled device (CCD) or a complementary metal-oxide semiconductor (CMOS) based device. The image sensor 38 may be monochromatic or color. The image sensor 38 generally has a small pixel size which is less than 9.0 μm in size and more particularly, smaller than 5.0 μm in size (e.g., 2.2 μm or smaller). Generally, sensors having smaller pixel size will produce higher resolutions.

The system 22 also includes a fluorescent excitation source 40 that is configured to emit radiation at one or more wavelengths for fluorescent excitation (e.g., fluorescent excitation source). The fluorescent excitation source 40 may include a LED or Xenon lamp tuned by a monochromator. The fluorescent excitation source 40 is preferably oriented at an angle with respect to the microfluidic device 10. The fluorescent radiation from the fluorescent excitation source 40 is delivered to the sample volume through a prism 42 (e.g. rhomboid prism). Located underneath the microfluidic device 10 is a layer of glass 44 that is used to reflect the excitation radiation through total internal reflection (TIR) surface 46. The layer of glass 44 may have a thickness on the order of about 100 μm. The image sensor 38 is disposed on the backside of the layer of glass 44 which is used to capture holographic images as well as fluorescent images. Interposed between the TIR glass layer 44 and the image sensor 38 is an adsorption filter 48. The adsorption filter 48 is generally thin having a thickness generally less than 100 μm.

After excitation of the cells or particles, the fluorescent radiation pump source is filtered out through total internal reflection (TIR) at the TIR surface 46. The same top or flat prism 42 interface also permits incoherent lensfree holography to be performed simultaneously for the same field of view. The center of mass of each fluorescent spot in lensfree images overlaps in 2D space with the fluorescent cell or particle's reconstructed holographic images, which enables separation of fluorescent particles from each other and from non-fluorescent ones within the same field of view. Additional details regarding holographic fluorescent imaging may be found in International Patent Application Publication No. WO 2011/049965, which is incorporated by reference fully herein. It should be noted that the prism 42 may be omitted in other embodiments of the system 22. For example, the microfluidic device 10 may be illuminated with the fluorescent excitation source 40 using side illumination (e.g., butt coupling) or even one or more wave guides (not shown).

Still referring to FIG. 1, the system 22 includes a computer 50 containing one or more processors 52 therein configured to process images acquired from the image sensor 38. Individual image frames that are captured from the image sensor 38 may be transmitted to and stored on the computer 50. The computer 50 may include software for image analysis. For example, the computer 50 may be loaded with imaging processing software such as IMAGEJ, a public domain JAVA image processing program, NIS Elements (Nikon Instruments, Inc., Melville, N.Y., USA). In the case of wide field-of-view without the use of any lenses, the computer 50 may contain software that acquires images of the cells or particles that include holographic amplitudes or intensities. The software on the computer 50 then recovers the lost phase image. Having both the holographic amplitude and recovered lost phase of the same image, the software then reconstructs an image of the cells or particles. The software may also be used to identify and display particular cells of interest. Moreover, as explained herein, the software may be used subtract images from one another to yield differential images based on the exposure to different fluorescent stains. The software may also be used to pseudo-color or false color features images obtained using different fluorescent stains. The software may also be able to form composite images made from multiple fluorescent images that are overlaid with one another.

Still referring to FIG. 1B, the computer 50 may have a monitor 54 that can display images or regions of interest, data, analysis results and the like to a user. Likewise the computer 50 may have one or more input device 56 such as a keyboard or the like. The computer 50 may be localized with the microfluidic device 10 or it may even be remote.

Figure 2:
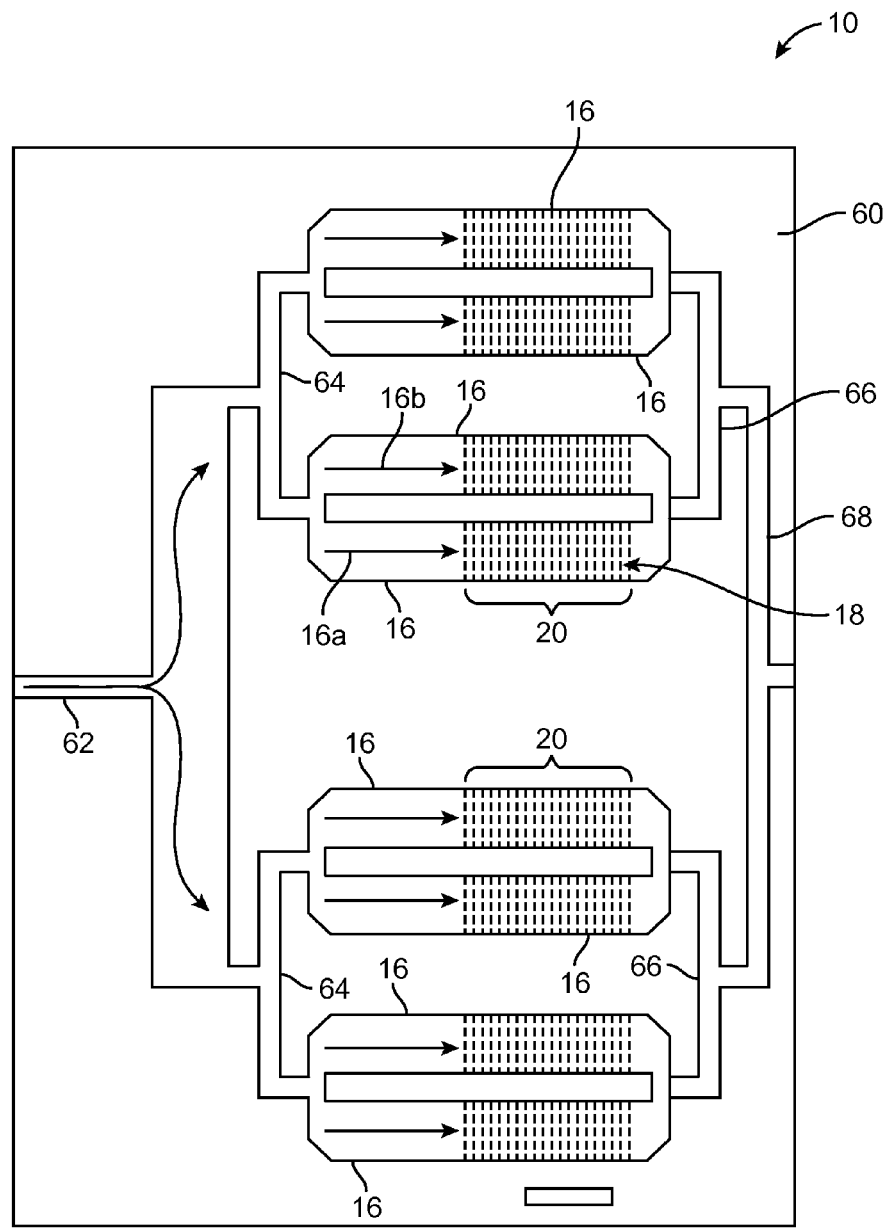
FIG. 2 illustrates another view of a microfluidic device that includes a plurality of chambers each having an array of traps therein.

FIG. 2 illustrates a magnified view of eight (8) separate flow chambers 16 (fluid flow are depicted by arrows 16a, 16b) with each chamber having an array 20 of traps 18 contained therein. The flow chambers 16 are disposed on or within a substrate 60. The substrate 60 can be any material useful for forming fluidic channels. A surface of the substrate 60 and/or the traps 18 may be modified to make it suitable for attachment of binding ligands (e.g., biological molecules). Substrates 60 useful in the device 10 include, but are not limited to, metal, glass, and plastic that may be used directly or may be modified with coatings (e.g., metals or polymers). The substrate 60 can be a metal, glass or silicon surface. In a one embodiment, the substrate can be made from a wide variety of materials, including, but not limited to, silicon such as silicon wafers, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terephthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, brass, sapphire, and the like. High quality glasses such as high melting borosilicate or fused silicas may be used for their UV transmission properties when any of the sample manipulation steps require light based technologies. In addition, portions of the device 10 may be coated with a variety of coatings as needed, to reduce non-specific binding, to allow the attachment of binding ligands, for biocompatibility, for flow resistance, and the like.

Still referring to FIG. 2, fluid with cells or particles (or wash fluid or fluid with a fluorescent stain) enters a common inlet branch channel 62 that splits into separate inlet channels 64 leading to pairs of common chambers 16. Each chamber 16 contains its own array 20 of traps 18. Each chamber 16 terminates at an outlet channel 66 that combines with other outlet channels to form a common outlet channel 68.

FIG. 3 illustrates a perspective view of a flow chamber 16 containing an array of traps 18 therein. A cover 70 is partially illustrated which resides some distance away from the traps 18 such that a small gap exists. The gap is small enough to permit the passage of fluid but not cells or particles. Individual cells 72 are shown held within each trap 18. As described further herein, traps 18 are located within the chamber 16 to substantially, but not fully, reduce fluid flow with in chamber 16. Traps 18 are designed to be of sufficient size to capture/trap cells or analytes within a fluid flowing through chamber 16. For example, where the distance between the substrate surface 60 in fluid contact and the cover surface 70 in fluid contact is 42 microns, the trap 18 extends into the fluid flow space of fluid chamber 16 a distance that would prevent a cell 72 from flowing over (or under) the trap 18. In the example, where the distance between substrate surface 60 and cover surface 70 is 42 microns, the trap 18 comprises a weir-trap height 74 that extends about 40 microns into the fluid flow space of the fluid chamber 16. Thus, approximately 2 microns remain as a reduced fluid flow space 76. In operation, the trap 18 is of sufficient depth into the flow space of chamber 16 to inhibit passage of the cell 72, while allowing fluid passage through reduced fluid flow space 76.

The traps 18 can be any shape which prevents passage of a cell 72 or particle while allowing fluid flow in a reduced fluid flow space 76 associated with the trap 18. For example, as depicted in FIG. 3, the traps 18 have concave shapes. Trapping array geometries are typically designed in a staggered fashion to optimize biological agent trapping as depicted in FIG. 3. With the geometries and flows it is possible to trap a plurality of biological agents in a trapping array 20.

Figure 4A:
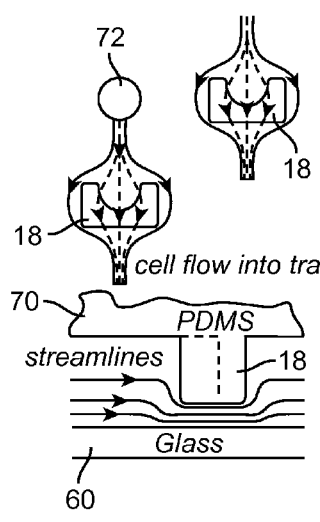
FIG. 4A illustrates top and side views, respectively, of the fluid flow streamlines flowing into and around a single trap that does not contain a trapped cell.
Figure 4B:
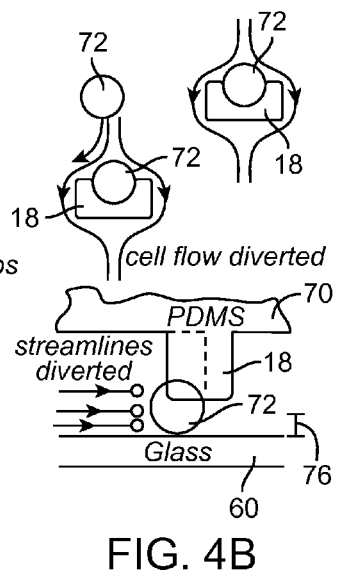
FIG. 4B illustrates top and side views, respectively, of the fluid flow streamlines flowing around a single trap that contains a trapped cell. The fluid streamlines are shown diverted.

The traps 18 may be formed on the substrate 60 or, alternatively, the traps 18 may be formed on the cover 70. FIG. 4A illustrates top and side views, respectively, of the fluid flow streamlines flowing into and around a single trap 18 that does not contain a trapped cell (though a cell 72 is shown immediately upstream of the trap 18). FIG. 4B illustrates top and side views, respectively, of the fluid flow streamlines flowing around a single trap 18 that contains a trapped cell 72. The fluid streamlines are shown diverted. In this embodiment, the traps 18 are formed in a cover 70 which is made of PDMS that is bonded to a substrate 60 made of glass.

Figure 5:
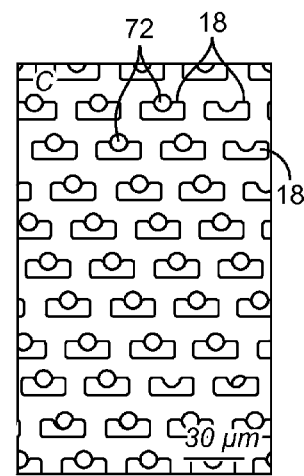
FIG. 5 illustrates a magnified plan view of a plurality of traps each holding individual cells.

FIG. 5 illustrates a magnified plan view of a plurality of traps 18 each holding individual cells 72 (some traps 18 do not have any cells 72).

Figure 6:
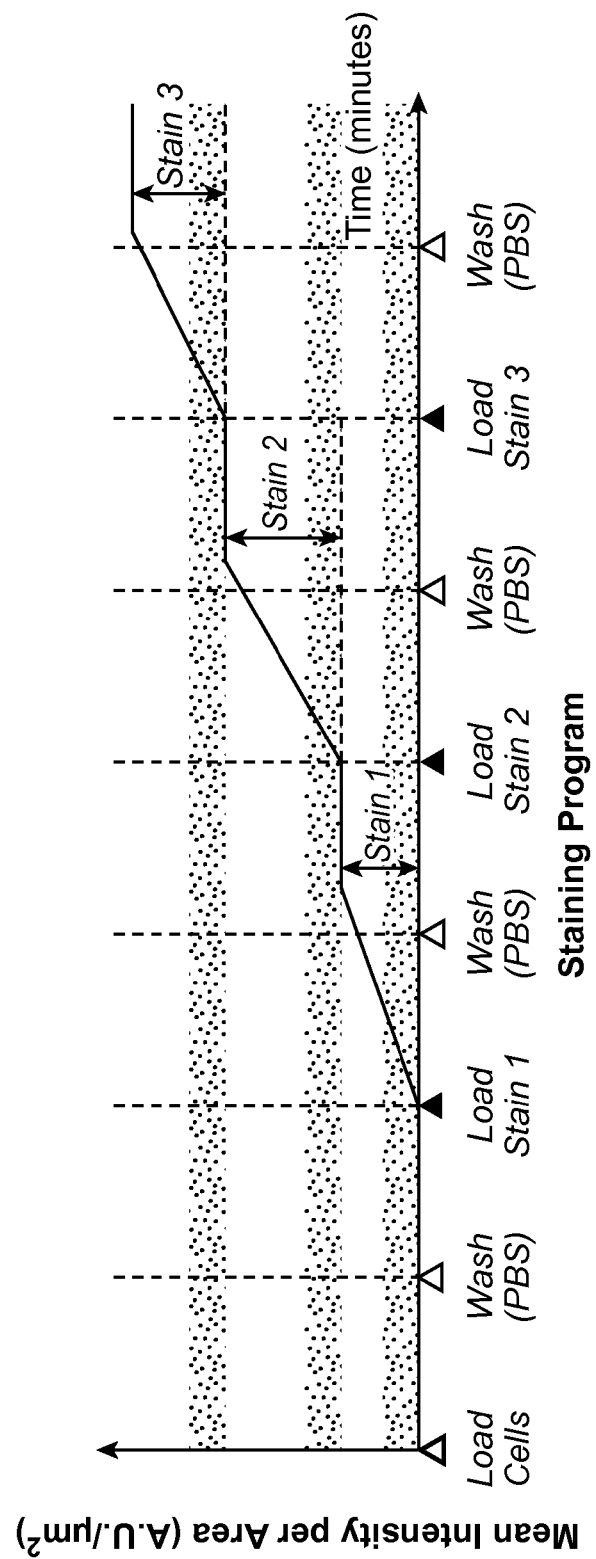
FIG. 6 illustrates an exemplary staining program of hydrodynamically trapped cells with three dyes that share fluorescent excitation and emission spectra. Bands of 4σ are illustrated for each stain. Mean fluorescent intensity per area is illustrated as increasing more than 4σ for each stain.

FIG. 6 illustrates an exemplary staining program of hydrodynamically trapped cells 72 with three fluorescent stains or dyes that share fluorescent excitation and emission spectra. That is the say the three fluorescent stains or dyes have a substantial overlap of the excitation and emission spectra (e.g., within same channel). Bands of 4 times the standard deviation ($\sigma$) of the measured mean intensity per area (A.U./$\mu m^2$) are illustrated for each fluorescent stain. In a typical program, a fluid containing cells 72 is loaded into the microfluidic device 10. With reference to FIG. 1B, the fluid containing the cells 72 may be pumped into (or pulled into) the inlet 12 via the pump 24. Typically, the traps 18 will fill with cells 72 within less than about a minute or so. A wash solution is then pumped through the microfluidic device 10. Next, a first fluorescent stain is flowed through the microfluidic device 10. Again, the stain may be pumped through the microfluidic device 10 using a pump 24. The first fluorescent stain may be a fluorophore that contains a binding moiety that selectively binds with a cell constituent. For example, the fluorophore may be conjugated with an antibody or the like that binds with a target antigen. For example, the fluorophore may target a specific cytological feature of the cell 72. For example, a particular fluorophore may target the cell cytoplasm, nucleus, organelle, cell surface, etc.

With reference to FIG. 1B, the fluorescent excitation source 40 is turned on to pump or excite the fluorophores that have bound to the cell 72. The fluorophores emit fluorescent light that is captured in images taken by the image sensor 38. The computer 50 preferably calculates the fluorescent intensity at each trapped cell 72. For example, imaging software contained in the computer 50 threshold images to discount cell debris and cell aggregates. The software then defines a region of interest (ROI) which represents the area of the cell. Once the software identifies the ROIs in the image, the software can then calculate for each image frame (or over multiple image frames) a mean fluorescent intensity per area (A.U./$\mu m^2$). As seen in FIG. 6, the mean fluorescent intensity increases as a function of time. Measurements of mean fluorescent intensity in FIG. 6 may be taken periodically with relatively short exposure times (less than 100 ms) to prevent bleaching of the image sensor 38.

Still referring to FIG. 6, a PBS wash solution is flowed through the device whereupon the mean fluorescent intensity per area plateaus or levels out. One or more image frames are captured during this plateau phase. This is important because the image frame (or multiple frames) taken during this phase are used during the subtraction operation that is performed (as explained in more detail below) to determine the differential fluorescent contribution from each subsequent fluorescent stain or dye that is flowed through the microfluidic device. For example, the arrow "Stain 1" of FIG. 6 represents the mean intensity contribution attributable to the first fluorescent stain. After the first plateau stage, a second fluorescent stain is flowed through the microfluidic device 10. Again, the stain may be pumped through the microfluidic device 10 using a pump 24. The second fluorescent stain may be a fluorophore that contains a binding moiety that selectively binds with a different cell constituent than the first fluorescent stain. For example, the first fluorescent stain may target the nucleus while the second fluorescent stain may bind with a target found in the cell cytoplasm.

As an alternative to image subtraction, the cells may be bleached completely before adding the next stain. Bleaching of the cell may be accomplished by exposure to light with very high power for a period of time to destroy the fluorophore.

Still referring to FIG. 6, in response to excitation radiation from the fluorescent excitation source 40, fluorophores that are bound to their target source emit fluorescent light that is captured in images taken by the image sensor 38. The mean fluorescent intensity per area increases again until a second wash solution (PBS) is flowed through the microfluidic device 10. After the second wash, the mean fluorescent intensity per area plateaus or levels off. One or more image frames are capture by the image sensor 38 throughout the process and particularly during this level phase. Using software loaded onto the computer (e.g., ImageJ), the mean fluorescent intensity during the first plateau may be subtracted from the mean fluorescent intensity during the second plateau. This differential is labeled by the arrow "Stain 2" in FIG. 6 and represents the contribution of the second fluorescent stain. This process can be repeated any number of times with additional fluorescent stains. For instance, in FIG. 6 a third fluorescent stain is applied followed by a wash (PBS). The mean fluorescent intensity per area increase after loading the microfluidic device 10 and then later plateaus or levels off following the addition of the PBS wash. Again, the mean fluorescent intensity during the second plateau may be subtracted from the mean fluorescent intensity during the third plateau. This differential is labeled by the arrow "Stain 3" in FIG. 6 and represents the contribution of the third fluorescent stain. The third fluorescent stain may target a different aspect of the cell 72. For example, the third fluorescent stain may target the cell surface.

Figure 7:
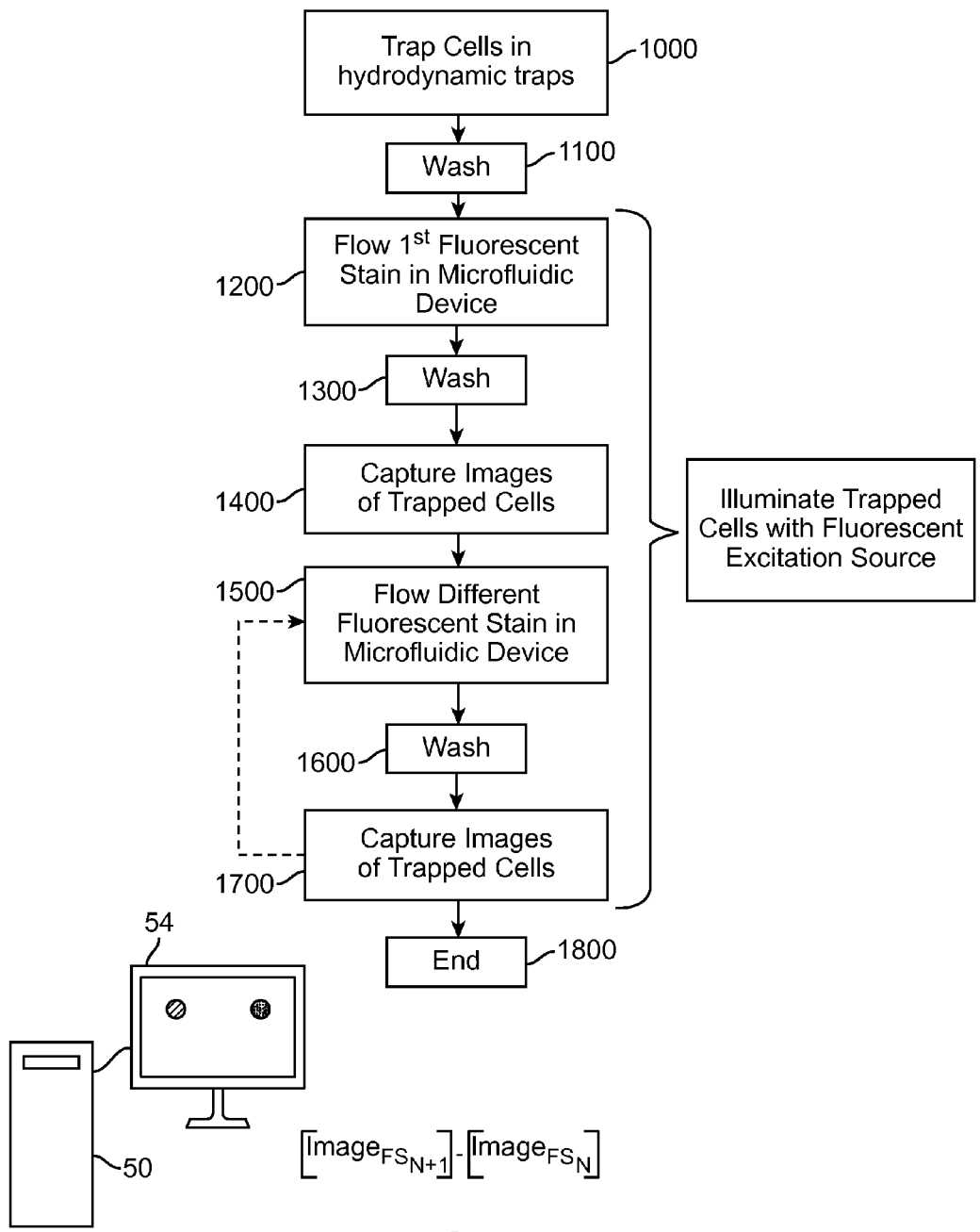
FIG. 7 illustrates a flow chart of exemplary steps used in a sequential array cytometry approaching using the hydrodynamically trapped cells.

FIG. 7 illustrates a flowchart illustrating a typical image acquisition process for the system 22. For instance, as seen in operation 1000 cells 72 are trapped within with traps 18. Next, in operation 1100 a wash solution (PBS) is flowed through the microfluidic device 10. A first fluorescent stain is flowed into the microfluidic device 10 in operation 1200 and subject to another wash operation 1300. The trapped cells 72 are illuminated with a fluorescent excitation source 40. One or more images are captured in operation 1400 during the plateau phase after wash operation 1300. The images may be captured by any number of ways. This can include, for example, a wide field-of-view imager such as the setup of FIG. 1B or it may include a fiber-optic array scanning imager, or a microlens imager.

Still referring to FIG. 7, a fluorescent stain selective to a different target (different fluorescent stain) is flowed through the microfluidic device 10 as seen in operation 1500. It is important to note that the different fluorescent stain includes the same or similar fluorophore as the first fluorescent stain the difference being that it is selective to a different target. In this regard, the different fluorescent stain has substantially the same excitation and emission spectrum as the first fluorescent stain. Another wash operation 1600 is performed and one or more images are captured in operation 1700 during the plateau phase after the washer operation 1600. Operations 1500 through 1700 are then repeated for any number of fluorescent stains. After the last stain has been flowed through the microfluidic device 10 the image acquisition process is complete 1800. Imaging can also be conducted throughout the staining and washing steps 1100 through 1700 in another embodiment.

The images that are captured from each stain are then transferred to the computer 50 for further processing and analysis. The computer 50 may analyze the spatial and temporal characteristics of the different fluorescent stains on each trapped cell 72 within the microfluidic device 10. For instance, the computer 50 may analyze how the fluorescent intensity changes over time. The computer 50 may also analyze the physical distribution of the fluorescent intensity in each cell 72. This spatial information may be combined with the temporal information to yield further information. As explained above, it is possible to quantify and image the relative contribution of each successive fluorescent stain that has been flowed through the microfluidic device 10. For instance, as seen in FIG. 7, the computer 50 may subtract an image taken during exposure of a subsequent fluorescent stain from an image taken during exposure of a prior fluorescent stain. This is represented by Equation 1 below wherein N refers to the number of fluorescent stains that are run through the microfluidic device and $Image_{FS}$ refers to the image taken upon exposure to the N or N+1 stain.

$$[Image_{FS\,N+1}]-[Image_{FS\,N}] \quad (1)$$

The computer 50 may perform additional analysis of the images. For example, the phenotypes of the trapped cells 72 may be determined based on the spatial and/or temporal information acquired during the image acquisition phase. Each additional fluorescent stain may provide additional information to narrow the list of potential cell types. For example, a series of multiple stains can be run through the microfluidic device 10 and the temporal and/or spatial response of each cell can be compared against a stored library to establish cell phenotypes. Quantitative measurements of intracellular and surface biomarkers as well as dynamic molecular events can be used to fingerprint cell phenotype. The computer 50 may also be used to present the user with images via the monitor 54 of the spatial and temporal impact of the various fluorescent stains. For example, as explained herein, prior images can be subtracted out to give the user an image that accurately reflects the contribution of a single fluorescent stain. These images may be pseudo-colored for better presentation purposes or the like. The images can even be overlaid with one another to form a composite image that one would typically expect from a multi-fluorophore protocol.

Experimental Results

To demonstrate the feasibility of sequential array cytometry three independent components of the ubiquitous HeLa cell line were stained in cells subject to hydrodynamic trapping. The contribution of the fluorescent signal from each fluorescent stain was extracted by image subtraction as described herein.

Microfluidic channels were fabricated by replica molding. A two-layer mold was constructed in SU-8 50 (MicroChem Corp., Newton, Mass., USA) using standard photolithographic methods. A transparent, elastomeric polymer, polydimethylsiloxane (PDMS; Sylgard 184 Silicone Elastomer, Dow Corning Corp., Midland, Mich., USA), was cast over the mold and cured at 65° C. for at least 3 hours. The PDMS could then be removed from the mold and inlet and outlet holes were punched with a pin vice assembly (Technical Innovations, Inc., Angleton, Tex., USA). The molded side of the PDMS and a slide glass were activated with air plasma for 30 seconds then placed in contact to form a permanent bond. Minimal pressure was applied to ensure contact, but care was observed to not collapse raised channel features onto the glass. The latter would prevent necessary flow through the hydrodynamic cell traps. The completed channels were left to bake at 65° C. for at least 5 minutes prior to use. Later, the inlet and outlet of the channel could be fitted with polymeric tubing and have fluid driven through them by a syringe pump. The top surface of the PDMS was sterilized with 70% ethanol then washed with sterile water.

Channels of the device were prefilled with 1× phosphate buffered saline (PBS) by injecting PBS through the outlet (outlet during the rest of the protocol) with a syringe pump at a flow rate of 20 μL/min. The inlet was obstructed with a metal pin during this time to eject air through the air-permeable PDMS walls. Subsequently, the pin was removed, and a 20-1L drop of PBS was loaded over the inlet. The flow direction on the syringe pump was reversed such that fluid was drawn from the drop through the channel. The drop was replenished before any air could enter the inlet. For cell loading, a suspension of cells was added dropwise to the inlet and the flow rate was reduced to 10 μL/min (optimized for cell trapping). For all other solutions and wash steps 10 μL/min was used.

The microfluidic channels were mounted on an inverted microscope stage and secured. Thus, while the experiments conducted using a conventional microscope it should be understood that other imaging modalities could be used including a wide field-of-view lens-free fluorescent imager, a fiber-optic array scanning imager, and a microlens imager. In fact, these are particularly well-suited for the system. The appropriate axial position and exposure times for the selected stains were chosen prior to experiments. Ambient light was minimized Grayscale fluorescent images were captured every 30 seconds using an automated time-lapse function in the image acquisition software (NIS Elements; Nikon Instruments Inc., Melville, N.Y., USA). In-between exposures the shutter was closed to minimize bleaching. Image processing was carried out in NIS Elements and ImageJ. The final image of the calcein AM staining process was used to identify the address and size of every cell within the imaged portion of the array. The mean intensity at every address in defined regions of interest (ROIs), which encompass the cell area at each address, was stored over time for kinetics experiments. For multi-parameter image reconstruction an image was selected from each staining step. The images were opened in ImageJ. Using the "Image Calculator" function sequential images were subtracted from one another to obtain only the staining that occurred during that interval. These were pseudo-colored different colors using the "Lookup Tables" function and overlaid in NIS Elements.

The fluorescent stain solutions used were 2 µM calcein AM (Invitrogen Corporation, Carlsbad, Calif., USA), 1.5 µM SYTO 16 green fluorescent nucleic acid stain (Invitrogen), and 25 µg/mL FITC-conjugated Lectin from Triticum vulgaris (wheat germ agglutinin; Sigma-Aldrich Corp., St. Louis, Mo., USA). Calcein AM is a cell-permeant and non-fluorescent compound that is widely used for determining cell viability. In live cells the non-fluorescent calcein, AM is hydrolyzed by intracellular esterases into the strongly green fluorescent anion calcein. The fluorescent calcein is well-retained in the cytoplasm in live cells. The cell-permeant SYTO 16 green fluorescent nucleic acid stain exhibits bright, green fluorescence upon binding to nucleic acids. FITC-conjugated Lectin from Triticum vulgaris is used for the fluorescent detection of glycoproteins containing $\beta(1\rightarrow4)$-N-acetyl-D-glucosamine The HeLa cell line (epithelial; human cervical adenocarcinoma) was propagated in Dulbecco's Modification of Eagle's Medium (DMEM) 19 with L-Glutamine, 4.5 g/L Glucose and Sodium Pyruvate, 10% fetal bovine serum (FBS), and 1% Penicillin/Streptomycin at 37° C. and 5% $CO_2$. Cells were released from tissue culture flasks with 0.25% Trypsin and re-suspended in their culture media. For measurements of noise and saturation limit 9.9 µm fluorescent polymer microspheres (Thermo Scientific, Waltham, Mass., USA) were used.

Figure 8:
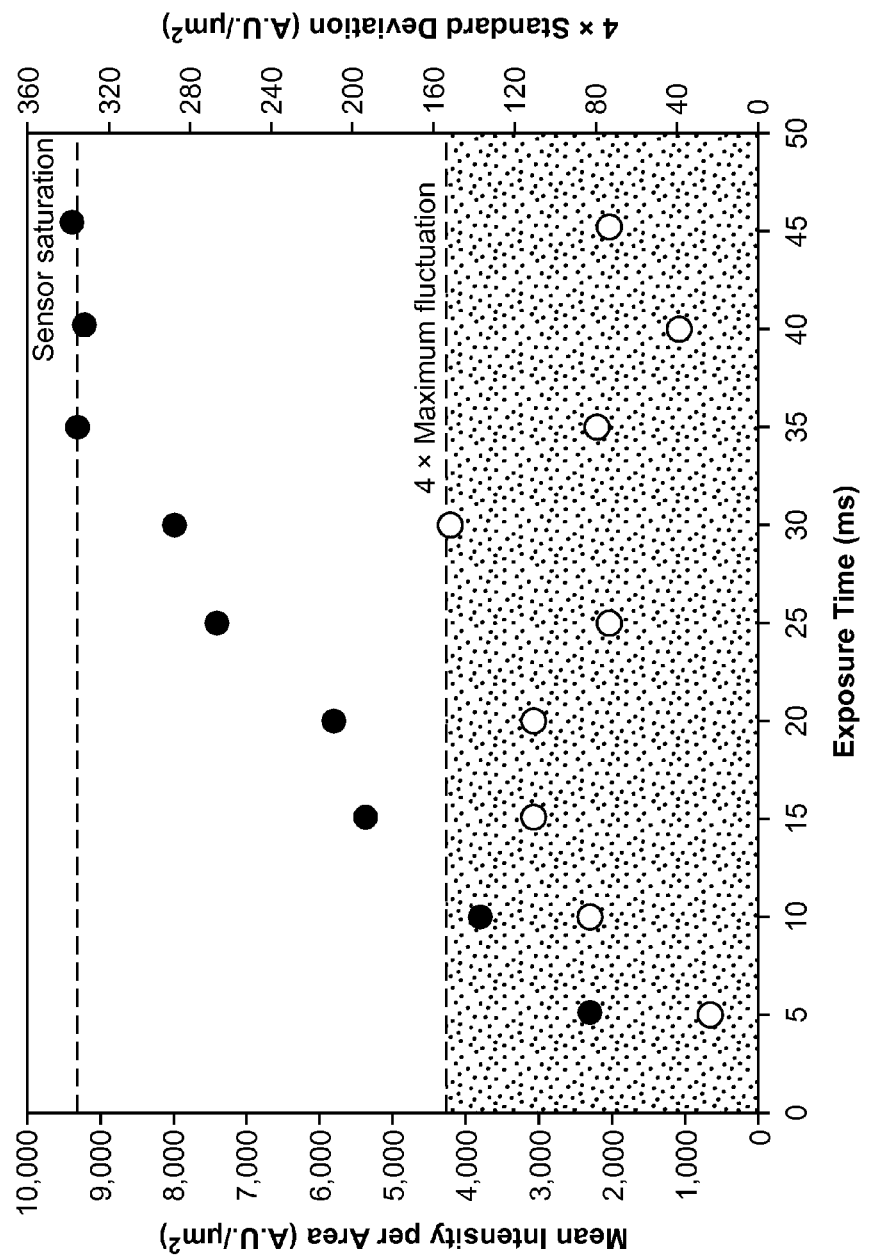
FIG. 8 illustrates a graph of the fluorescent intensity (mean intensity per area) of non-bleaching 9.9 µm fluorescent polymer microspheres captured every 30 seconds for 3 minutes at nine (9) exposure times ranging from 5 to 45 ms. Also illustrated (right hand axis) is indication of 4 times the maximum standard deviation of the mean (4σ).

The number of independent parameters that can be measured within a single fluorescent channel is limited by the noise and the number of grayscale levels before saturation for the detection scheme. Non-bleaching fluorescent polymer microspheres were hydrodynamically trapped and their mean fluorescent intensity per area was measured every 30 seconds for 3 minutes (experimental conditions identical to subsequent cell-based assays) at nine exposure times from 5 to 45 ms. As seen in FIG. 8 the mean fluorescent intensity per area (N=8 particles) increases with exposure time until the sensor's limit is reached, defining the saturation limit (Mean ~9300 AU/µm$^2$). The maximum standard deviation of the mean, $\sigma$, in this range of exposure times was 39 AU/µm$^2$. A practical definition of the noise is $4\sigma$; thus staining increments should be larger than $4\sigma$ to unambiguously resolve these levels above background noise (FIG. 6 illustrates horizontal bands equal to $4\sigma$ for each stain). For the experiments illustrated in FIG. 6, each staining procedure resulted in an intensity increment greater than 1000 AU/µm$^2$.

The mean intensity per area for each cell was extracted from the images at every time point. A two-tailed t-test assuming unequal variances was carried out comparing the mean of control and experimental conditions.

Figure 9A:
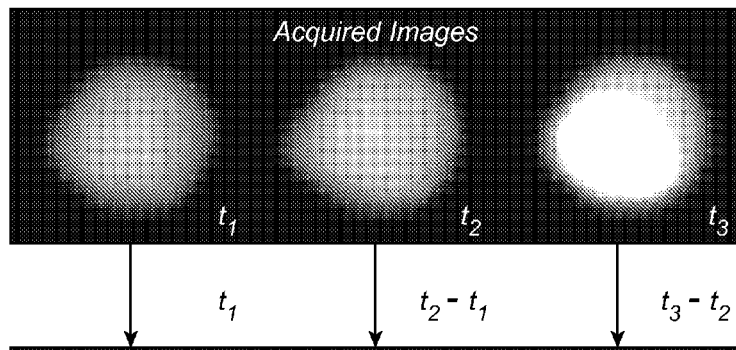
FIG. 9A illustrates fluorescent images of a single cell being exposed to three fluorescent stains having substantially the same excitation and emission properties. Images are taken at $t_1$, $t_2$, and $t_3$.

To demonstrate the feasibility of sequential array cytometry three independent components of the ubiquitous HeLa cell line (hydrodynamically trapped within an array) were stained with all fluorescein spectrum dyes and extracted the contribution to the fluorescent signal from each molecular probe by image subtraction. Fluorescent images were recorded throughout the program with the shutter closed in between images to prevent bleaching. The important frames are those where fluorescence intensity has become level; these occur during the wash steps after each stain (FIG. 6). One frame from each wash step was selected for the image calculations. Microscopic fluorescent images were taken with a 10x objective and a single filter. FIG. 9A illustrates images with pixels expanded 1000%.

Figure 9B:
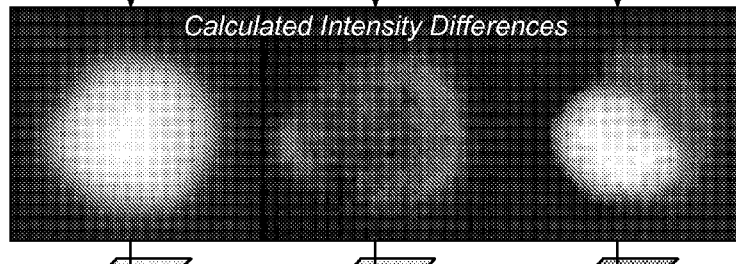
FIG. 9B illustrates the fluorescent image intensity differences obtained by subtracting the most recent fluorescent image intensity (e.g., $t_1-t_0$, $t_2-t_1$, $t_3-t_2$).
Figure 9C:
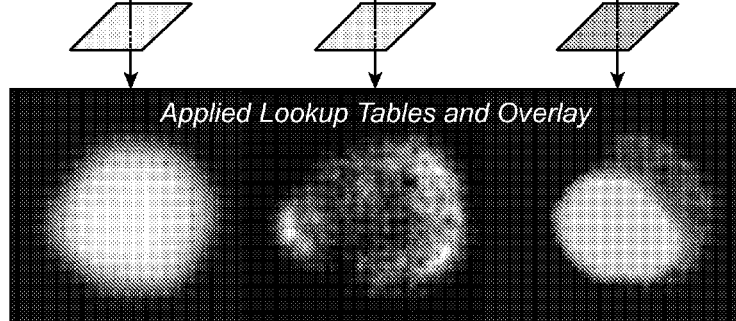
FIG. 9C illustrates the subtracted images being pseudo-colored.
Figure 9D:
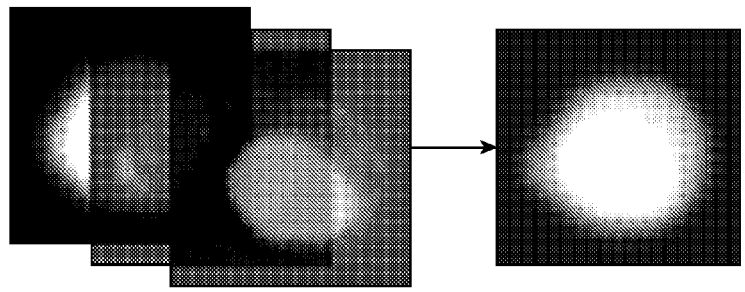
FIG. 9D illustrates the scaling of the intensity of the pseudo-colored images which are then overlaid for a composite multi-parameter image.

Calcein AM is cleaved by internal carboxyl esterases to fluorescent calcein and is typically used as a live cell indicator as it diffuses through the plasma membrane. It is located throughout the cytosol. The left image in FIG. 9A illustrates the acquired image frame taken during the wash after exposure to Calcein AM. A FITC-conjugate of wheat germ agglutinin binds glycoconjugates, typically found on the surface of the cell. The center image in FIG. 9A illustrates the acquired image frame taken during the wash after exposure to FITC-conjugate of wheat germ agglutinin. Lastly, SYTO 16 stains nucleic acids in the nucleus and mitochondria and is seen in the acquired image (right most image) of FIG. 9A. The calculated difference between fluorescence intensities between these images reveals what was contributed by the subsequent stain. FIG. 9B illustrates the subtracted images that represent the contribution of each stain. These new images were adjusted for brightness and pseudo-colored as seen in FIG. 9C images. These images where then overlaid as seen in FIG. 9D to create what one would typically expect from a multi-fluorophore staining protocol.

To characterize the dynamics of drug transporters at the single-cell level, Caco-2 cells were trapped and perfused with calcein AM. The increase in emitted fluorescence with time was then quantified. The Caco-2 (epithelial; human colorectal adenocarcinoma) cell line was propagated in DMEM 19 with L-Glutamine, 4.5 g/L Glucose and Sodium Pyruvate, 20% FBS, and 1% Penicillin/Streptomycin at 37° C. and 5% carbon dioxide ($CO_2$). Cells were released from tissue culture flasks with 0.25% Trypsin and re-suspended in their culture media. The microfluidic device used in connection with this experiment is the same as described above for the HeLa cell experiment. Cells were either inhibited or uninhibited. 100 µM fluoxetine (Cerilliant Corporation, Round Rock, Tex., USA) was used as an inhibitor of drug-resistance transporters.

Figure 10:
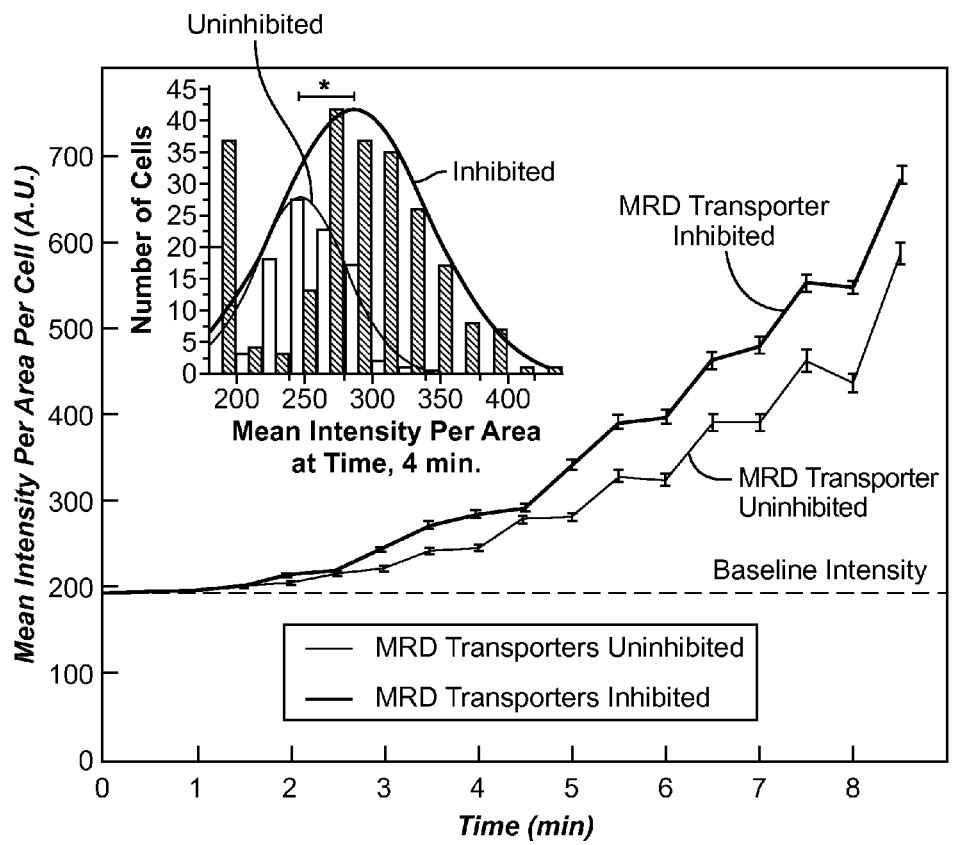
FIG. 10 illustrates a graph of the measured mean intensity per area per cell as a function of time for Caco-2 cells which were inhibited or not inhibited. A histogram shows the distribution of mean intensities per area after 4 minutes (inset).

The rate of increase in the emitted fluorescence is reduced by efflux of calcein AM by MDR transporters such as MDR-1. In a separate condition we first exchanged the solution around the cells to 100 µM fluoxetine, a known inhibitor of these transporters, then replaced it with 2 µM calcein AM/100 µM fluoxetine. The single-cell fluorescence increase was quantified over 8.5 min as seen in FIG. 10. Statistical tests demonstrate statistical significance of the difference between inhibited (N=232) and uninhibited populations (N=112) after 4 min. A histogram (inset in FIG. 10) illustrates the distribution of single-cell data, identifying a non-normal distribution. As rare cells can dominate clinical outcomes (e.g., rare drug-resistant cells leading to cancer relapse) the ability to identify a whole population distribution is critical but cannot be achieved with bulk measurements. The portion of the cells at the baseline intensity can be removed by software as they were late to enter the trapping region. While the dynamics of drug efflux are not thoroughly used here, this device and method have the ability to extract kinetic information after having already stained the cell (i.e., when the cells do not share the same baseline intensity values).

An additional area where the microfluidic device 10 and methods may be used is the development of enzyme profiles of single cells. Here, sequential probing is performed for a variety of enzymes using fluorogenic substrates. Unique fingerprints for various cell types allows for easy discrimination with reduced cost compared to antibody-based techniques. Various enzymes can be probed in parallel by applying the various fluorogenic substrates in a sequential manner, and considering the baseline fluorescent level from the previous reaction. In this way, one could use a cell's enzyme profile in a diagnostic manner. A particular application is in determining variations of enzymes involved in drug metabolism and prodrug activation across patient populations, such as cytochrome P450 and carboxylesterases. One could then understand and tailor drugs to the specific metabolic enzyme profile of a patient. Having an enzyme profile for single cells would help greatly in distinguishing cells in different disease states. For example, this can be applied to differentiating circulating tumor cells from normal circulating cells.

FIGS. 11A-11C illustrate one method of performing single cell enzyme profiling. As seen in FIG. 11A, a first enzyme substrate that is non-fluorescent (e.g., carboxylesterase) is exchanged with a plurality of hydrodynamically trapped cells. A wash solution is exchanged with the trapped cells (FIG. 11B) and is followed by another exchange with a second enzyme substrate (e.g., cytochrome P450). This cycle is repeated any number of times represented by arrow A with a different enzyme substrate. FIG. 11D schematically illustrates an enzyme substrate reacting with an intracellular enzyme to form a fluorescent product. The fluorescent intensity may be monitored as a function of time as described previously herein. FIG. 11E illustrates fluorescent intensity graphs as a function of time for three different cell types being sequentially exposed to three different enzyme substrates. FIG. 11F illustrates a similarity matrix of various cell types. It should be understood that other intracellularly-converted fluorogenic substrates can be monitored such as calcein AM, FDA, cytochrome P450 substrates, protease substrates, galactosidase substrates, and the like for cell phenotyping and classification.

The system 22 and methods described herein offer a massively parallel sequential cytometry solution. The device uses a single fluorescent excitation source as well as a single filter. There is no need for multiple excitation sources or filters. Solutions of fluorescent stains and washes can be rapidly exchanged with single cells. Several thousand (up to around 30,000 cells/cm$^2$ can be trapped and observed. The system 22 in one embodiment may incorporate a wide field-of-view lens-free fluorescent imager 30 that can be used to obtain both bright field images of cells as well as fluorescent images.

The system 22 and methods offer an inexpensive alternative to high-end multi-color flow cytometers with additional information content and reduced sample preparation difficulty. Spatial and temporal dynamics of many individual cells may be monitored and analyzed. The system 22 has the potential to measure up to 60 independent parameters which is several times more than current state-of-the-art flow cytometers. When coupled with wide view imaging techniques the system can be used for personalized high content screening (e.g., testing drug efficacy with subject's own cells).

While embodiments have been shown and described, various modifications may be made without departing from the scope of the inventive concepts disclosed herein. The invention(s), therefore, should not be limited, except to the following claims, and their equivalents.

What is claimed is:

1. A method of monitoring temporal and spatial information of eukaryotic cells comprising:
    a) trapping a plurality of disassociated eukaryotic cells within single cell traps contained in a microfluidic device having an inlet, and an outlet;
    b) flowing a first fluorescent stain specific to a first target into the inlet of the device;
    c) flowing a wash solution into the inlet of the device to remove the first fluorescent stain that is not bound to the eukaryotic cells;
    d) imaging the plurality of trapped eukaryotic cells one or more times after flowing the wash solution in (c), wherein imaging occurs at a filtered wavelength range consisting of a single color;
    e) identifying one or more regions of interest in the one or more images obtained in (d) using a processor executing imaging software and quantifying the fluorescent intensity of the one or more regions corresponding to light emitted by the first fluorescent stain;
    f) flowing a second fluorescent stain specific to a different target into the inlet of the device, wherein the first fluorescent stain remains bound to the first target;
    g) flowing a wash solution into the inlet of the device to remove the second fluorescent stain that is not bound to the eukaryotic cells;
    h) imaging the plurality of trapped eukaryotic cells one or more times at the filtered wavelength range consisting of a single color;
    i) identifying one or more regions of interest in the one or more images obtained in (h) using a processor executing imaging software and quantifying the fluorescent intensity of the one or more regions corresponding to light emitted by the first and second fluorescent stains; and
    j) using the processor executing imaging software to subtract the quantified fluorescent intensity obtained in operation (i) from the quantified fluorescent intensity obtained in operation (e).

2. The method of claim 1, wherein the single cell trap comprises a hydrodynamic single cell trap.

3. The method of claim 1, further comprising:
    k) flowing a third fluorescent stain specific to a different target into the inlet of the device, wherein the first and second fluorescent stains remain bound, respectively, to the first target and the second target;
    l) flowing a wash solution into the inlet of the device to remove the third fluorescent stain that is not bound to the eukaryotic cells;
    m) imaging the plurality of trapped eukaryotic cells one or more times at the filtered wavelength range consisting of a single color;
    n) identifying one or more regions of interest in the one or more images obtained in (m) using a processor executing imaging software and quantifying the fluorescent intensity of the one or more regions corresponding to light emitted by the first, second, and third fluorescent stains; and
    o) using the processor executing imaging software to subtract the quantified fluorescent intensity obtained in operation (n) from the quantified fluorescent intensity obtained in operations (i) and (e).

4. The method of claim 1, further comprising the processor executing software for pseudo-coloring an image corresponding to the subtracted fluorescent intensity.

5. The method of claim 4, further comprising the processor executing software for pseudo-coloring an image corresponding to the fluorescent intensity of an image obtained during operation (i).

6. The method of claim 1, further comprising the processor executing software for extracting kinetic information based at least in part on the change in fluorescent intensity of the first or second fluorescent stains as a function of time.

7. The method of claim 1, wherein imaging the plurality of trapped cells in operations (e) and (i) comprises measuring the mean fluorescent intensity of the region of interest.

8. The method of claim 1, wherein the plurality of trapped cells are imaged a plurality of times in operations (e) and (i) using an imager selected from the group comprising a wide field-of-view lens-free fluorescent imager, a fiber-optic array scanning imager, and a microlens imager.

9. The method of claim 1, wherein the first target is located in a first region of a eukaryotic cell and the different target is located in a different region of the eukaryotic cell.

10. The method of claim 9, wherein the first region and different region comprise one or more of cell nucleus, cell cytoplasm, and cell surface.

11. The method of claim 1, wherein at least one of the first target and the different target comprise an enzyme.

12. The method of claim 1, wherein imaging comprises capturing fluorescent light passing through a single optical filter.

13. The method of claim 3, further comprising the processor executing software for identifying the phenotype of one or more eukaryotic cells of the plurality based on spatial and/or temporal information obtained during the imaging operations.

14. The method of claim 3, further comprising the processor executing software for generating a composite image based on the quantified fluorescent intensity for each fluorescent stain.

15. The method of claim 1, wherein the first fluorescent stain in operation (b) and the second fluorescent stain in operation (f) are the same.

16. The method of claim 1, wherein the first fluorescent stain in operation (b) and the second fluorescent stain in operation (f) emit the same color light.

17. A method of monitoring temporal and spatial information of eukaryotic cells comprising:

a) trapping a plurality of disassociated eukaryotic cells within single cell traps contained in a microfluidic device having an inlet and an outlet;

b) sequentially flowing different fluorescent stains that bind to different targets of the eukaryotic cells into the inlet of the device, wherein each of the sequentially flowed different fluorescent stains remain bound to target and are not washed from the target prior to the delivery of a next fluorescent stain;

c) imaging the plurality of trapped eukaryotic cells after each different fluorescent stain is flowed through the microfluidic device, wherein imaging occurs at a filtered wavelength range consisting of a single color;

d) identifying one or more regions of interest in the one or more images obtained in (c) using a processor executing imaging software and quantifying the fluorescent intensity of the one or more regions using light emitted by a cumulative sum of each different fluorescent stain; and e) using the processor executing imaging software to obtain the difference between the quantified fluorescent intensity following a prior stain from the quantified fluorescent intensity following a subsequently added stain of the sequentially flowed different fluorescent stains.

* * * * *